(12) United States Patent
Martel et al.

(10) Patent No.: US 8,641,965 B2
(45) Date of Patent: Feb. 4, 2014

(54) METHOD AND DEVICE FOR CONTROLLING THE STERILIZATION OF PRODUCTS IN AN AUTOCLAVE

(75) Inventors: Paul Martel, St. Raphael (FR); Guy Charvin, Antibes (FR)

(73) Assignee: MXM, Vallauris (FR)

( * ) Notice: Subject to any disclaimer, the term of this patent is extended or adjusted under 35 U.S.C. 154(b) by 1684 days.

(21) Appl. No.: 11/700,637

(22) Filed: Jan. 31, 2007

(65) Prior Publication Data

US 2007/0202004 A1    Aug. 30, 2007

(30) Foreign Application Priority Data

Feb. 2, 2006    (FR) ...................................... 06 00964

(51) Int. Cl.

| | |
|---|---|
| *A61L 2/24* | (2006.01) |
| *A61L 2/00* | (2006.01) |
| *A61L 2/04* | (2006.01) |
| *A61L 9/00* | (2006.01) |
| *A61L 11/00* | (2006.01) |
| *C23F 11/00* | (2006.01) |
| *B65D 69/00* | (2006.01) |
| *B65D 71/00* | (2006.01) |

(52) U.S. Cl.
USPC ................................... 422/3; 422/1; 206/569

(58) Field of Classification Search
USPC .......................................... 422/1, 3; 206/569
See application file for complete search history.

(56) References Cited

U.S. PATENT DOCUMENTS

| | | | |
|---|---|---|---|
| 3,982,893 A | 9/1976 | Joslyn | |
| 4,728,504 A * | 3/1988 | Nichols | ......................... 422/297 |
| 4,865,814 A * | 9/1989 | Childress | ...................... 422/116 |
| 5,426,428 A | 6/1995 | Binder et al. | |
| 2003/0133830 A1 | 7/2003 | Gonzalez et al. | |

FOREIGN PATENT DOCUMENTS

| | | |
|---|---|---|
| DE | 298 02 948 | 10/1998 |
| DE | 198 25 166 | 12/1999 |
| GB | 1 163 917 | 9/1969 |
| WO | WO 01/07092 | 2/2001 |

\* cited by examiner

*Primary Examiner* — Regina M Yoo
(74) *Attorney, Agent, or Firm* — Bachman & LaPointe, P.C.

(57) ABSTRACT

Method for controlling the sterilization of products in an autoclave, in which products are placed in at least one closed, unsealed and confined container of any type, and according to which inside this same container there is a loaded and autonomous device for measuring in the container at least one sterilization parameter wherein during at least one part of the duration of the sterilization cycle and according to a predefined frequency, at least one representative value of the measurement of the at least one parameter is recorded in the loaded device and at least one of these representative values is transmitted directly through the container that remains closed, through wireless transmission by electromagnetic rays of waves with a frequency of less than 250,000 GHz.

19 Claims, 2 Drawing Sheets

METHOD AND DEVICE FOR CONTROLLING THE STERILIZATION OF PRODUCTS IN AN AUTOCLAVE

BACKGROUND

This invention relates to a method and device for controlling the sterilization of products in an autoclave.

The technical sector of the invention is the domain for controlling the sterilization cycles performed in devices, in particular, closed, pre-evacuation- and sterilizing gas-type instruments, in order to verify if the sterilization cycle is performed under the correct conditions.

This invention, in particular but not exclusively, is designed to be used in pre-evacuation devices for sterilization by water vapor such as the autoclaves ensuring the sterilization of medical and hospital equipment and for which it is even more necessary to know whether they have been effectively and correctly sterilized, such as, for example, by exposure to water vapor at 134° Celsius for 18 minutes. And these conditions must be satisfied even inside the containers in which this equipment is placed and that are designed to preserve the sterile status of the latter until they are used after they are removed from the autoclave.

These containers are therefore designed, on the one hand, to prevent the penetration of any liquids or other contaminants during storage and transport to the location in which they are opened in order to use the products that they contain, and, on the other, to be sufficiently unsealed to allow vacuum and entry of liquid, such as vapor, for sterilization using pressure differentials created by the pre-vacuum of the container during the sterilization cycle in the autoclave: this is obtained either by exhaust valve systems that open in one direction and another when the external pressure in the container is sufficiently different from the internal pressure in order to allow the vacuum in one direction, and in the other, allow the input of the sterilization liquid such as vapor, or by reducing the communication openings between their internal and external volume, and protecting these openings either mechanically or by various filters such as paper filters that close them, these various elements allow qualifying the internal volume of these containers as "confined" and complement the unsealed characteristic.

As an example, this "unsealed" and confinement characteristic will be defined by a passage section surface value authorized by these filters with respect to the internal volume of the containers equal to at least 0.1% $M^{-1}$, and preferably 0.5% $M^{-1}$ and possibly more, but still remaining very low, in order to allow the vacuum, then the input of sterilization vapor liquid within a reasonable amount of time that is compatible with the total duration of a sterilization cycle.

Currently, this type of control of the "correct" sterilization of products contained in a container (that is, for example, that their temperature has been maintained between 121 and 134° Celsius for 3 to 25 minutes, and/or that the pressure variation according to the temperature has correctly followed the equilibrium curve of saturating vapor, called the Regnault curve) can only be performed upon opening the container in order to use the equipment placed inside it, that are supposed to have been correctly sterilized: for this purpose, one places, before their closure and introduction into the autoclave, inside each container, either a sufficiently large and loaded equipment capable of continuously measuring and recording the temperature and pressure or a vapor reactive physiochemical ink indicator, which is checked at the time of opening.

This check is nevertheless pushed back for a long time after sterilization, so that the container may be moved to the location of its use that may be far away from the autoclave; thus in cases of non-compliance, the equipment cannot be used, and it must therefore be sent for re-sterilization, which wastes time and requires the availability of significant advance stock of equipment that have undergone the sterilization cycle and are waiting to be used in order to make up for the risk of the incorrect sterilization of some of them.

The problem presented is therefore to be able to control this at the earliest time possible, either before or right after the containers are removed from the autoclave, even if it is well in advance of using the equipment that they contain, while subsequently preserving the sterilization of the latter until it is used, without needing to use a product and/or a complicated, time-consuming and/or costly method; and this control must be able to be done with all existing unsealed and confined containers, in particular those that are completely made of metal without special adjustments such as a transparent window, as described in the German utility model DE 29802948.

SUMMARY OF THE INVENTION

A solution to the problem presented is a sterilization control method of products in an autoclave, in which these products are placed in at least one closed unsealed and confined container, of any type suitable for sterilization such as that defined above, either entirely metallic and/or with opaque walls, and according to which in this same container there is available a loaded and independent device for measuring in said container at least one sterilization parameter and so that in said loaded device, during at least one part of the sterilization cycle duration and according to a predefined frequency, at least one representative value of at least said parameter is recorded.

According to the invention, at least one of these representative values is transmitted directly by the loaded device and through the closed container by using electromagnetic wave transmission at a frequency of less than 250,000 GHz, preferably below 30,000 GHz, and even 1,000 GHz, and which can go up to expansive hertzian waves of 3 KHz while passing through all the hertzian waves called radioelectric waves comprised between 9 KHz and 3,000 GHz, such as microwaves, UHF, VHF, HF, MF, LF, and VLF, or by magnetic induction.

Taking into account that many containers are made of metal, such as those manufactured by the company WAGNER Gmbh and sold under the brand name STERISET®, and the fact that their characteristically low sealability, which gives wall continuity in the envelope of these containers, a person skilled in the art would consider such transmission through the latter as impossible due to the FARADAY cage effect: the inventor of this invention has therefore overcome this preconception and has perfected various methods such as those described below in order to simplify to the fullest the acquisition of data and to only have to transmit a minimum amount of information, which thus reduces the size, capacities and operating batteries of the device that can implement such methods, thus simplifying its implementation and reducing the manufacturing costs.

In particular, such a device is therefore not only a recording instrument in the sense that it does not record and maintain all the data collected during the sterilization cycle: these are methoded locally within the device and are then lost, and it is only the result(s) of this methoding that is/are recorded and transmitted at the end of the sterilization cycle and upon request to an external reader such as the one defined below.

Through the method of the invention as presented above and described in more detail below, one can read, with an external reader that can receive hertzian waves or that can capture the magnetic induction emitted by the device according to the invention, without the container needing specific adjustment such as a transparent window or external antenna, and without having to open the containers before or upon removing them from the autoclave, the data stored in the devices according to the invention, previously placed inside the latter: the external reader therefore allows the operator to check, by controlling the transmitted representative values of the measurement of the measured and recorded parameter(s), whether the sterilization cycle has been carried out correctly inside the container, according to preset criteria; and if these have not been satisfied, the operator can therefore immediately check whether there is a problem with the container (such as blocked filters or other problems) and place it inside the autoclave for another sterilization cycle.

Only the containers that have correctly undergone the compliant sterilization cycle are therefore sent to potential users who will be able to open them when desired and who can be sure that they will find equipment that has been sterilized correctly.

The result is new methods and devices for controlling the sterilization of products in an autoclave that respond to the problem of controlling the quality of sterilization, at the earliest either before or after removing the containers from the autoclave, while preserving the sterilization of the products and equipment contained inside the containers, since there is no longer a need to open them in order to perform the check, and this can be done with a simple and economical device, as described more specifically below as an example using any type of existing unsealed and confined container, in particular those made of metal and/or opaque walls.

BRIEF DESCRIPTION OF THE DRAWINGS

Other advantages of this invention can be described, but those described above provide sufficient indication to demonstrate the innovation and interest. The description and diagrams attached represent an example embodiment of the invention, but are in no way limiting: other embodiments are possible within the framework of the scope and reach of this invention.

DETAILED DESCRIPTION OF THE PREFERRED EMBODIMENT(S)

Figure 1:
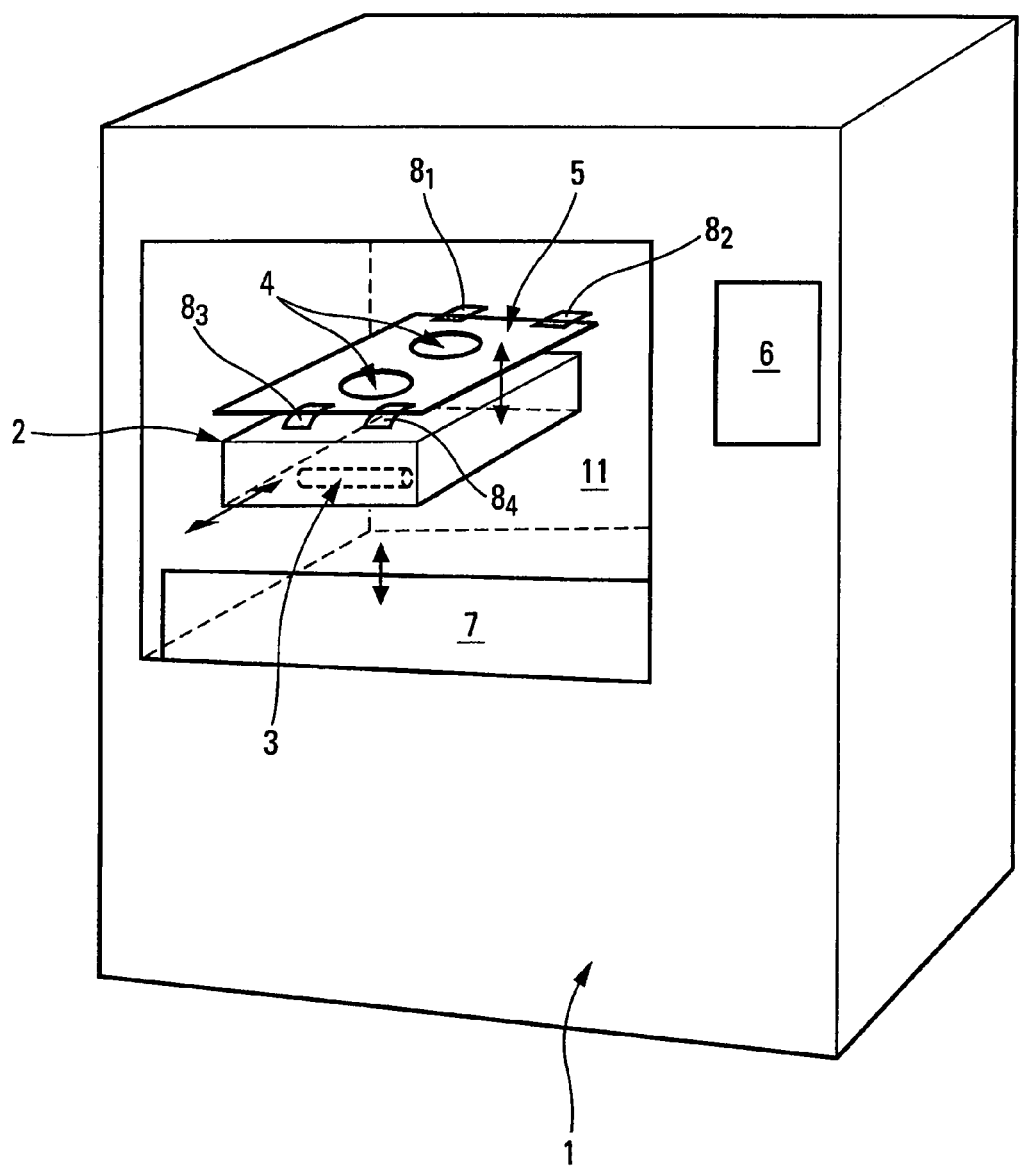
FIG. 1 is a full top view of a container that can be filled with products or equipment to be sterilized and of a device according to the invention, ready to be closed and inserted into an autoclave in order to undergo a sterilization cycle.

Placed inside at least one unsealed and confined closed container 2, of any type suitable for sterilization, are products that one wishes to sterilize and a loaded autonomous device 3 for measuring 12 in said container 2 of at least one sterilization parameter.

Said container includes at least one unsealed, but not transparent, wall section 4, which is generally held by the lid 5 and that is composed of paper-type filters that have the previously defined characteristics.

Said lid 5 is closed and locked on the base of the container using various closing systems 8. Said container is therefore placed inside the sterilization chamber 11 of an autoclave 1 and one can place several containers side by side and one on top of the other, each of which encloses equipment or products to be sterilized as well as a loaded device 3 according to the invention. The access and locking door 7 of the autoclave 1 can then be closed and the sterilization cycle can be started using a command console 6.

Figure 2:
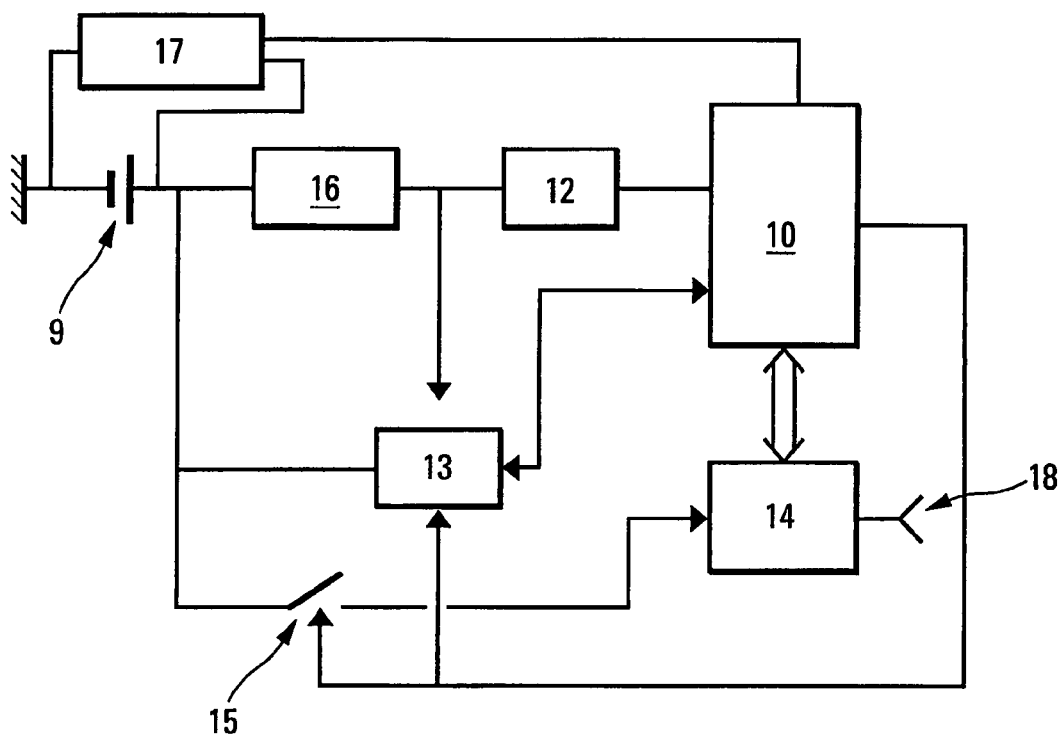
FIG. 2 is an electronic and electrical diagram of a component circuit that constitutes a device according to the invention.

Using the loaded device 3, represented in FIG. 2, one can record into a memory 13 during at least one part of the duration of the sterilization cycle and according to a predefine period of time, at least one representative value of the measurement of said obtained parameter using a sensor 12.

Using a transmitter 14 at least one of these representative values is then transmitted through the closed container 2 either when the latter is still in the autoclave 1 and at any time during the sterilization cycle or directly after the container 2 is extracted from inside the autoclave 1, or sometime later. Preferably, the at least representative value is only transmitted at the end of the sterilization cycle and one can deduce the way in which this sterilization cycle has been performed.

To do so, said representative value of the measurement is transmitted to an external reader not represented in the Figures that can gather the representative values of measurements from several devices 3, each placed simultaneously in a different container 2; thus, each of the containers placed together in an autoclave 1 in order to undergo the same sterilization cycle includes a device 3 for which the control of the measurements obtained can be performed at the end of the sterilization cycle using a single reader.

During the sterilization cycle, during which the measurement of the parameter(s) is performed, the emission 14 can be deactivated using a switch 15 that does not deactivate until the temperature in the container falls below a certain temperature, for example room temperature, indicating that the sterilization cycle has been completed and that the container has been removed from the autoclave.

Inversely, another service switch 16 is only deactivated when the temperature measured inside the container has exceeded a minimum threshold, for example 100° Celsius; such a switch 16 can be composed of a thermal switch.

Device 3 is autonomous, contains electrical batteries 9 and an electronic component circuit, in which at least one of these components 10 is programmed to execute the method according to this invention, in which the device can be placed inside said container 2 in order to measure at least one sterilization parameter.

The external envelope of the device is permeable to electromagnetic rays or magnetic induction.

The electronic component circuit includes an analog-digital converter 10 placed as far forward as possible near the sensor 12 that can measure the at least sterilization parameter; said electronic components circuit can also auto-calibrate the measurement sensor 12.

The device 1 also includes a battery 9 tester 17 and uses wireless transmission 18 through electromagnetic rays of waves with a frequency of less than 250,000 GHz, preferably below 30,000 GHz, and even 1,000 GHz, and which can go up to expansive hertzian waves of 3 KHz while passing through all the hertzian waves called radioelectric waves comprised between 9 KHz and 3,000 GHz, such as microwaves, UHF, VHF, HF, MF, LF, and VLF or through magnetic induction.

In a specific embodiment, one can also use the variation of temperature inside the container 2 in order to create an electrical current that can recharge the battery 9 of this device, but this option is not represented in FIG. 2.

In order to minimize the size of the memory 13 and to have to transmit only a minimum of data at the end of the cycle, as the measurements 12 are made of said at least one parameter in the loaded device 3, taking into account at least one of the measurement values and those previously recorded, all predefined calculations 10 are performed, such as the example provided below, which allows obtaining a new representative value of said measurement and the last value thus calculated is recorded 13 instead of the previous one, which allows erasing the previously recorded value(s).

In a specific embodiment, the method of the invention is such that:
- in said loaded device throughout the duration of the sterilization cycle, the value of at least one measured parameter is compared 10 to at least one predetermined parameter,
- when at least this last value is obtained, this information is gathered as valid and constitutes the representative value of the measurement of said at least one parameter,
- then, said data is transmitted 14 either before or after the container 2 is extracted from inside the autoclave 1 and through the container 2 that has remained closed, and
- it is deduced that the sterilization cycle has been performed correctly in the minimum satisfactory conditions.

In a preferred embodiment, the comparison of the values and the recording of the data that is valid and representative of this measurement performed in the loaded device 3, said data is obtained and transmitted in binary form.

The predetermined value of the measured parameter is, for example, a threshold such as pressure, humidity or temperature and, the valid data is obtained when, on the one hand, the value of said parameter measured by the sensor 12 (taking into account that there can be several if several of these parameters are to be measured: pressure, humidity, temperature) has reached this threshold, and on the other hand, only after the value of this parameter is maintained above this threshold for a given time.

In another embodiment, the Regnault curve is considered as a set of predetermined values of the temperature to be controlled within the area according to the pressure, one compares 10, during the sterilization cycle, the values measured of the temperature and pressure in the container 3 with the values of said curve, and the validation data is obtained 13 when these measured values correspond to those of the Regnault curve for a given time.

Furthermore, because in general the at least one measured parameter in said container may be temperature, the sterilization force $F_0$ is calculated at all times, as $F_0 = \int temp * dl$ and the value obtained is transmitted in the form of a digit.

Through the simplicity of the method according to the invention and of the electronic diagram of the device represented in FIG. 2, the latter can be miniaturized and slid into an external envelope in the form of a cylinder with a diameter of 3 cm and a length of between 12 and 15 cm, for example, a plastic tube closed at both ends.

The invention claimed is:

1. A method for controlling sterilization of products in an autoclave, comprising:
   placing the products for sterilization in at least one closed, unsealed and confined container having a base portion;
   providing a lid having at least one unsealed wall section with a passage section surface value with respect to an internal volume of said at least one container equal to at least 0.1% $M^{-1}$ to allow a vacuum and then an input of sterilization vapor fluid into the at least one container within a period of time compatible with a total duration of a sterilization cycle;
   loading inside said container an autonomous device for measuring in said container at least one sterilization parameter that is recorded in said loaded autonomous device during at least part of the total duration of the sterilization cycle and according to a predefined frequency, at least one representative value of a measurement of said at least one parameter;
   attaching said lid to said base portion after said autonomous device has been loaded into said at least one container; and
   transmitting said at least one representative value directly through the at least one container that remains closed, and said transmitting step comprising using a wireless transmission by electromagnetic rays of waves with a frequency of less than 250,000 GHz or through magnetic induction.

2. The method for controlling sterilization according to claim 1, wherein said transmitting step comprises transmitting said at least one of the representative values through the at least one container that remains closed, only at the end of the sterilization cycle.

3. The method for controlling sterilization according to claim 1, wherein said placing step comprises placing the products in a container made of metal.

4. The method according to claim 1, wherein, as measurements are obtained of the at least one parameter in the loaded autonomous device, taking into account at least a last measurement value and a previously recorded one, performing a calculation that allows obtaining a new representative value of said measurement, and recording a last value thus calculated in place of the previous one.

5. The method according to claim 4, further comprising in said loaded autonomous device throughout the duration of the sterilization cycle, comparing the value of at least one measured parameter to at least one predetermined parameter, and when at least said last value is obtained, gathering information as valid and constituting the representative value of the measurement of said at least one parameter, then transmitting the representative value after the at least one container is extracted from inside the autoclave and through the at least one container that has remained closed, and deducing that the sterilization cycle has been performed correctly in the minimum satisfactory conditions.

6. The method according to claim 5, further comprising performing the measurement of the at least one parameter, the comparison of the values, and the recording of the representative value that is valid and representative of the measurement in the loaded autonomous device, obtaining said representative value, and transmitting said representative value in binary form.

7. The method according to claim 6, wherein the predetermined value of the measured parameter is a threshold, and obtaining the valid data when, on the one hand, the value of said parameter reaches said threshold and, on the other hand, only after the value of said parameter is maintained above said threshold for a given time.

8. The method according to claim 7, further comprising considering a Regnault curve as a set of predetermined values of the temperature to be controlled within the area according to pressure, comparing measured values during the sterilization cycle of the temperature and pressure in the at least one container with the values of said Regnault curve, and obtaining validation data when said measured values correspond to those of the Regnault curve during a given time.

9. The method according to claim 8, wherein the at least one measured parameter in said at least one container is temperature, and calculating a sterilization force $F_0$ at all times, as $F_0 = \int temp * dl$ and transmitting the value obtained in the form of a digit.

10. The method according to claim 9, further comprising transmitting said representative value of the measurement to an external reader that can gather the representative values of the measurements of several devices each placed simultaneously in a container.

11. The method according to claim 10, further comprising using temperature variation inside the container to create an electrical current that can recharge a battery of the autonomous device.

12. The method according to claim 1, further comprising using hertzian waves to perform the wireless transmission through electromagnetic rays.

13. The method according to claim 12, wherein said hertzian wave using step comprises using a frequency of 800 MHz.

14. The method according to claim 12, wherein said hertzian wave using step comprises using a frequency of 2.4 GHz.

15. A device for controlling sterilization of equipment in an autoclave, in which products are placed in at least one closed, unsealed and confined container having a lid, a base portion to which the lid is attachable, and at least one unsealed wall section held by the lid, said at least one unsealed wall section having a passage section surface value with respect to an internal volume of said at least one container equal to at least 0.1% $M^{-1}$ to allow a vacuum and then an input of sterilization vapor fluid into the at least one container within a period of time compatible with a total duration of a sterilization cycle, the device being autonomous with electrical batteries and an electronic component circuit, and able to be placed inside said at least one container in order to measure inside said at least one container at least one sterilization parameter, wherein at least one electronic component is programmed to execute the method according to claim 1.

16. The device according to claim 15, wherein an external envelope is permeable to an electromagnetic ray or wireless magnetic induction.

17. The device according to claim 15, wherein the electronic component circuit comprises an analog-digital converter placed as far forward as possible near a sensor able to measure the at least sterilization parameter.

18. The device according to claim 17, wherein said electronic component circuit is configured to auto-calibrate the sensor of at least one sterilization parameter.

19. A method for controlling sterilization of products in an autoclave, comprising:
placing the products to be sterilized in at least one closed, unsealed and confined container having a lid and at least one unsealed wall section held by the lid;
providing an autonomous device for measuring at least one sterilization parameter, which autonomous device has a sensor for measuring said at least one sterilization parameter, and an electronic component circuit including an analog-digital converter placed near the sensor and being capable of auto-calibrating the sensor;
loading inside said at least one container said autonomous device for measuring and recording said at least one sterilization parameter during at least part of a duration of a sterilization cycle and according to a predefined frequency, at least one representative value of a measurement of said at least one parameter; and
wirelessly transmitting said at least one representative value directly through the container in which said autonomous device is located while the container remains closed so as to determined whether sterilization of products in that container has been completed, and said wireless transmission step comprising using a wireless transmission by electromagnetic rays of waves with a frequency of less than 250,000 GHz or through magnetic induction.

* * * * *